United States Patent [19]

Paul

[11] 4,265,907
[45] May 5, 1981

[54] INSECTICIDAL HYDROXYLAMINE ETHERS

[75] Inventor: Jill H. Paul, Edgewater, N.J.

[73] Assignee: Mobil Oil Corporation, New York, N.Y.

[21] Appl. No.: 108,925

[22] Filed: Dec. 31, 1979

[51] Int. Cl.$^3$ .................... A01N 37/34; C07C 127/19
[52] U.S. Cl. ................................. 424/304; 260/465 E; 424/300; 424/316; 424/320; 424/322; 424/330; 564/50; 564/51; 564/52; 564/103; 564/300
[58] Field of Search ............ 260/570.9, 553 A, 561 B, 260/562 P; 424/320, 322, 324, 330, 316, 300, 304

[56] References Cited

U.S. PATENT DOCUMENTS

| | | | |
|---|---|---|---|
| 3,635,974 | 1/1972 | Freter et al. | 260/570.9 |
| 3,732,299 | 5/1973 | Levine et al. | 260/570.9 X |
| 4,084,003 | 4/1978 | Nadelson | 260/570.9 X |
| 4,108,897 | 8/1978 | Henry | 260/570.8 |

Primary Examiner—Robert V. Hines
Attorney, Agent, or Firm—Charles A. Huggett; James F. Powers, Jr.; Hastings S. Trigg

[57] ABSTRACT

Insecticidal compounds having the formula:

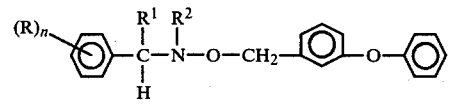

wherein R is halogen (Cl, F, Br), $C_1$–$C_4$ alkyl, $NO_2$, $C_1$–$C_4$ alkoxy, $C_1$–$C_4$ alkylthio, cyano, $CF_3$, $CF_3O$, $CF_3S$, $ClF_2$, $CHF_2O$, or $CHF_2S$; n is 0, 1, or 2; $R_1$ is $C_1$–$C_4$ alkyl, $C_3$–$C_6$ cycloalkyl, or $C_2$–$C_4$ alkenyl; and $R^2$ is hydrogen, cyano, formyl, $C_1$–$C_4$ acyl, $C_1$–$C_4$ carboalkoxy, carbamoyl, N-$C_1$–$C_4$ alkylcarbamoyl, or N,N-di $C_1$–$C_4$ alkylcarbamoyl.

9 Claims, No Drawings

INSECTICIDAL HYDROXYLAMINE ETHERS

BACKGROUND OF THE INVENTION

1. Field of the Invention

This invention is concerned with hydroxylamine ethers having insecticidal activity.

2. Description of the Prior Art

In U.S. Pat. No. 4,108,897, it is disclosed that useful insecticidal properties are possessed by hydroxylamine ethers of the formula:

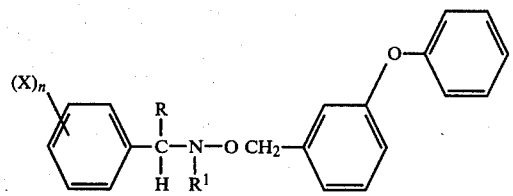

wherein n is 0, 1, or 2, X is lower halogen, and R is hydrogen or alkyl of from 1 to 6 carbon atoms, and $R^1$ is hydrogen or alkyl of from 1 to 6 carbon atoms. Such compounds are outside the scope of the present invention.

SUMMARY OF THE INVENTION

This invention provides insecticidal compounds having the formula:

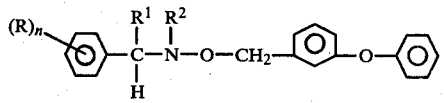

wherein R is halogen (Cl, F, Br), $C_1$–$C_4$ alkyl, $NO_2$, $C_1$–$C_4$ alkoxy, $C_1$–$C_4$ alkylthio, cyano, $CF_3$, $CF_3O$, $CF_3S$, $CClF_2$, $CHF_2O$, or $CHF_2S$; n is 0, 1, or 2; $R_1$ is $C_1$–$C_4$ alkyl, $C_3$–$C_6$ cycloalkyl, alkyl substituted $C_3$–$C_6$ cycloalkyl, or $C_2$–$C_4$ alkenyl; and $R^2$ is hydrogen, cyano, formyl, $C_1$–$C_4$ acyl, $C_1$–$C_4$ carboalkoxy, carbamoyl, N-$C_1$–$C_4$ alkylcarbamoyl, or N,N-di $C_1$–$C_4$ alkylcarbamoyl.

DESCRIPTION OF SPECIFIC EMBODIMENTS

Non-limiting examples of the compounds of this invention include:

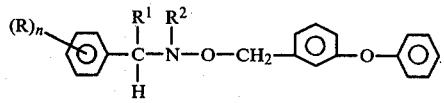

| n | R | $R^1$ | $R^2$ |
|---|---|---|---|
| 1 | 4-Cl | cyclopropyl | CHO |
| 1 | 4-$CF_3$ | isopropyl | acetyl |
| 1 | 4-$CF_3$ | methylcyclopropyl | CHO |
| 2 | 2-CL,4-$CF_3$ | isopropyl | CHO |
| 1 | 4-$CF_3O$ | cyclopropyl | CHO |
| 1 | 4-$CF_3S$ | cyclopropyl | CHO |
| 1 | 4-$CF_2Cl$ | cyclopropyl | CHO |
| 1 | 4-$CHF_2O$ | cyclopropyl | CHO |
| 1 | 4-$CHF_2S$ | cyclopropyl | CHO |
| 1 | 4-$CF_3$ | isopropyl | H |
| 1 | 3-$CF_3$ | isopropyl | acetyl |
| 1 | 4-$CF_3O$ | cyclopropyl | N-methylcarbamoyl |
| 1 | 4-$CF_3$ | cyclopropyl | N,N-dipropylcarbamoyl |
| 1 | 4-$CF_3O$ | cyclopropyl | propionyl |
| 1 | 4-$CF_3$ | cyclobutyl | N-methylcarbamoyl |
| 1 | 4-$CF_3$ | isobutenyl | CHO |
| 1 | 4-$CF_3O$ | isobutenyl | CHO |
| 2 | 2-Cl,4-F | isopropyl | acetyl |
| 2 | 2-Br,4-Br | isopropyl | acetyl |
| 2 | 2-Cl,4-$CF_3$ | cyclopropyl | CHO |
| 2 | 2-Cl,4-$CF_3$ | cyclopropyl | acetyl |
| 1 | 4-$CF_3$ | cyclopropyl | H |

SYNTHESIS METHODS

In general, the compounds of this invention are prepared by two methods:

(a) Condensation of an aryl alkyl ketoxime with 3-phenoxybenzyl bromide in the presence of a base and a suitable solvent (general procedure E), followed by hydrogenation (general procedure G) and N-substitution (general procedure H).

(b) Condensation of an isolated alkali metal ketoximate salt with 3-phenoxybenzyl bromide in an appropriate solvent (general procedure F), followed by hydrogenation (general procedure G) and N-substitution (general procedure H).

The ketoximes are prepared from aryl alkyl ketones and hydroxylamine hydrochloride in a manner familiar to those skilled in the art and according to general procedure D.

The aryl ketones are obtained from commercial sources or are synthesized from available aromatics and carboxylic acid chlorides or from a benzonitrile and a Grignard reagent, as described in general procedures A, and C.

3-Phenoxybenzyl bromide is obtained from commercial sources or can be synthesized from available alcohols and a halogenating agent (e.g. phosphorous tribromide) in a manner familiar to those skilled in the art.

GENERAL PROCEDURE A FOR ARYL ALKYL KETONES

A solution of 3.0 mole of the substituted benzene and 0.8 mole of alkyl acid chloride is cooled to $-5°$ C. Aluminum chloride (0.9 mole) is added portionwise, with vigorous stirring, while maintaining the reaction temperature at 0° C. The reaction mixture is brought to room temperature and allowed to stir overnight, whereupon the whole is poured into 450 ml. of concentrated HCl and 1200 ml. of ice-$H_2O$. The aqueous mixture is extracted two times with 350 ml. portions of $CHCl_3$. The combined organic extracts are washed with 5% NaOH, $H_2O$, dried over $MgSO_4$, and concentrated under reduced pressure. The residue is distilled via short path to obtain 0.64–0.68 mole of pure product.

GENERAL PROCEDURE C FOR ARYL ALKYL KETONES

Typical Example

Preparation of m-Methyl Isobutyrophenone

A solution of 23.4 g (0.2 mole) of m-methylbenzonitrile in 50 ml. of dry tetrahydrofuran is cooled to 10° C. A 2.2 M solution (90 ml., 0.2 mole) of isopropyl magnesium chloride in ether is added dropwise, while maintaining the reaction temperature below 30° C. The ether is removed (by distillation) and the reaction mixture heated to 70° C. for 4 hours. Upon cooling to room temperature, 100 ml. of aqueous 6 N HCl is added dropwise. Reaction mixture is refluxed for 2 hours. The resulting two layers are separated and the aqueous layer is extracted three times with 200 ml. portions of ether. The combined extracts are washed once with H$_2$O, once with saturated NaHCO$_3$ and once again with H$_2$O, dried over MgSO$_4$ and concentrated under reduced pressure. The residue is distilled using a vigreux column to obtain 23.6 g. (73% yield) of pure product.

4-Trifluoromethylcyclopropiophenone is generally prepared similarly, but using p-trifluoromethylphenyl magnesium bromide and cyclopropanecarbonitrile.

GENERAL PROCEDURE D FOR KETONE OXIMES

In general, the aryl alkyl ketones prepared by general procedures A, and C were dissolved in ethanol and refluxed 3–5 hours in the presence of an excess of hydroxylamine hydrochloride and potassium hydroxide. The reaction mixture is concentrated and the oxime or its potassium salt is extracted into an organic solvent or H$_2$O, followed by acidification with concentrated HCl, respectively. Recrystallization from either hexane, hexane/CHCl$_2$ or EtOH/H$_2$O followed.

GENERAL PROCEDURE E FOR OXIMINOETHERS

In general, 0.02 mole of the ketone oximes prepared by general procedure D were dissolved in 10 ml of toluene and added dropwise to a slurry of 0.02 mole of NaH (57% in mineral oil) in 10 ml. toluene and 4 ml. of DMF. The mixture is warmed to ~50° C. until H$_2$ evolution ceases, whereupon 0.02 mole of 3-phenoxybenzyl bromide is added dropwise at ~30° C. The reaction mixture is stirred overnight at room temperature and quenched by addition of 50 ml. of H$_2$O and 100 ml. of toluene. The organic layer is washed with 5%, 50:50 aqueous/ethanol NaOH, followed by H$_2$O, dried over MgSO$_4$, and concentrated under reduced pressure to yield 0.015–0.017 mole of crude product. Chromatography on silica gel, using 50:50 CH$_2$Cl$_2$/hexane as eluent, provides a highly purified product.

GENERAL PROCEDURE F FOR OXIMINOETHERS

A solution of 0.02 mole of ketoxime in 20 ml. of ethanol is added to a freshly prepared ethanolic solution of 0.02 mole NaOEt. The mixture is stirred at room temperature for 30 minutes and concentrated under reduced pressure to dryness. The resulting sodium oximate salt is dissolved in a minimum volume of 90% DMF and 10% t-butanol, whereupon 0.02 mole of 3-phenoxybenzyl bromide (neat) is added dropwise, causing an exotherm of ~8° C. The reaction mixture is stirred overnight at room temperature and poured into H$_2$O. The resulting oil is extracted two times into toluene. The combined organic layers are washed with 5% NaOH (50:50 H$_2$O/ethanol) H$_2$O, dried over MgSO$_4$, and concentrated under reduced pressure to yield 0.15–0.19 mole of >90% pure product.

GENERAL PROCEDURE G FOR HYDROGENATION

The oximinoethers are hydrogenated (reduced) with sodium cyanohydridoborate under acid conditions according to the procedure described in J. Am. Chem. Soc., 93, 2897–2904 (1971). The oximinoether is mixed with the borate in a suitable solvent, such as methanol, an acid, such as hydrochloride acid, and an indicator which changes color at about pH 4. As hydrogen ion is consumed during the reaction, additional acid is added to maintain the acidity of the reaction mixture. The whole is concentrated and quenched with H$_2$O, the resulting product recovered and purified using conventional techniques, such as extraction, crystallization, chromatography and the like.

GENERAL PROCEDURE H FOR N-SUBSTITUTION

The hydroxylamine ethers can be N-substituted with acyl, carboalkoxy, carbamoyl, N-alkylcarbamoyl, or N,N-dialkylcarbamoyl group by reaction, respectively, with an acyl chloride, e.g., acetyl chloride, propionyl chloride; an alkyl chloroformate, e.g., ethyl chloroformate, isopropyl chloroformate, isobutyl chloroformate; N-alkyl carbamoyl chloride, e.g., N-methyl carbamoyl chloride, N-isopropyl carbamoyl chloride; or N-alkyl isocyanate; e.g., methyl isocyanate, isopropyl isocyanate; or an N,N-dialkyl carbamoyl chloride, e.g., N,N-diethyl carbamoyl chloride, N,N-dipropyl carbamoyl chloride. The reactions are well known and involve splitting out HCl in the presence of a tertiary amine, e.g., pyridine, triethylamine.

The N-substitution of a formyl group is illustrated in Example 1.

EXAMPLE 1

Commencing with chlorobenzene and isobutyryl chloride and following general procedures A, D, and F, 1-(4-chlorophenyl)-2-methyl-1-propanone, 0-(3-phenoxyphenyl)methyl oxime was prepared. Using general procedure G, this material was hydrogenated to form 4-chloro-alpha(1-methylethyl)-N-(3-phenoxyphenyl)-methoxy)benzenemethanamine.

The latter amine (1.9 g., 0.005 mole) and 12.5 ml. formic acid were placed in a reaction flask and cooled to 5° C. Acetic anhydride (4 ml.) was added dropwise, allowing the reaction mixture to warm to room temperature. On reaching room temperature, there was an exotherm to 36° C. After the exotherm subsided, the temperature was increased to 50° C. and held for 2 hours. The reaction was stirred at room temperature overnight. Then, it was poured into water and extracted with diethyl ether. The ether extract was washed with water; 10% NaOH; water and dried over MgSO$_4$ and stripped of ether to get an oil; 4-chloro-N-formyl-alpha(1-methylethyl)-N-(3-phenoxyphenyl)methoxy)-benzenemethanamine.

EXAMPLE 2

Commencing with chlorobenzene and cyclopropanecarboxylic acid chloride and following general procedures A, D, and F, 1-(4-chlorophenyl)-2-methyl-1-cyclopropanone, 0-(3-phenoxyphenyl)methyl oxime was prepared. This oxime was hydrogenated using general procedure G and then reacted with methyl isocyanate, using general procedure H, to form 4-chloro-N-(N-methylcarbamoyl)-alpha-cyclopropyl-N-(3-phenoxyphenyl)methoxy)benzenemethanamine.

EXAMPLE 3

Similarly as described in Example 2, but using isopropyl isocyanate, there was prepared 4-chloro-N-(N-isopropylcarbamoyl)-alpha-cyclopropyl-N-(3-phenoxyphenyl)methoxy)benzenemethanamine.

The compounds of this invention have been found to exhibit considerable biological activity. They are especially potent pesticides when used to control or combat important agricultural pests. These compounds can be used in various ways to achieve biological action. They can be applied per se, as solids or in vaporized form, but are preferably applied as the toxic components in pesticidal compositions of the compound and a carrier. The compositions can be applied as dusts, as liquid sprays, or as gas-propelled sprays and can contain, in addition to a carrier, additives such as emulsifying agents, wetting agents, binding agents, gases compressed to the liquid state, odorants, stabilizers and the like. A wide variety of liquid and solid carriers can be used in the pesticidal compositions. Non-limiting examples of liquid carriers include water; organic solvents such as alcohols, ketones, amides, and esters; mineral oils such as kerosene, light oils, and medium oils, and vegetable oils such as cottonseed oil. Non-limiting examples of solid carriers include talc, bentonite, diatomaceous earth, pyrophyllite, fullers earth, gypsum, flours derived from cottonseeds and nut shells, and various natural and synthetic clays having a pH not exceeding about 9.5.

The amount of the compounds of this invention utilized in pesticidal compositions will vary rather widely. It depends to some extent upon the type of composition in which the material is being used, the nature of the condition to be controlled, and the method of application (i.e., spraying, dusting, etc.). In the ultimate pesticidal composition, as applied in the field, pesticide concentrations as low as 0.0001 weight percent of the total composition can be used. In general, compositions, as applied, containing about 0.05 weight percent pesticide in either liquid or solid carrier, give excellent results. In some cases, however, stronger dosages up to about 10 weight percent may be required.

In practice, pesticidal compositions are usually prepared in the form of concentrates, which are diluted in the field to the concentration desired for application. For example, the concentrate can be a wettable powder containing large amounts of the compound of this invention, a carrier (e.g., attapulgite or other clay), and wetting and dispersing agents. Such powders can be diluted prior to application, by dispersing it in water to obtain a sprayable suspension containing the concentration of pesticide desired for application. Other concentrates can be solutions that can be later diluted, e.g., with kerosene. Thus, it is within the contemplation of this invention to provide pesticidal compositions containing up to about 80%, by weight of the composition, of a pesticidal compound of this invention. Accordingly, depending upon whether it is ready for application or it is in concentrated form, the contemplated pesticidal compositions contain between about 0.0001 percent and about 80 percent, by weight of the compositions, of a pesticidal compound of this invention and a carrier, liquid or solid, as defined hereinbefore.

INSECTICIDE TEST METHODS

Bait Test [Housefly (Adult)]

Method of Treatment

One milliliter of an aqueous solution or suspension of the candidate compound is pipetted into a 9 cm. petri dish containing filter paper and 0.1 gm. granular sugar. Ten adults are admitted and the dish is closed.

Method of Recording Results

Mortality is recorded after 24–75 hours. Compounds which produce 90% mortality are reevaluated at lower concentrations in secondary tests. Mode of action may be by stomach poison, contact or vapor.

Stomach Poison–Foliar Dip Test

Primary Screen

Southern Armyworm (Larva)
Mexican Bean Beetle (Larva)

Method of Treatment

Lima bean leaves of a uniform size are momentarily dipped in a 500 ppm. water-acetone of the test material. Treated leaves are placed on moistened filter paper in 9 cm. petri dishes and allowed to air dry, and then are infested. The dishes are then closed.

Method of Recording Results

Mortality is recorded 72 hours after infestation. Compounds active at 500 ppm. are retested at 100 and 10 ppm.

All test results are recorded as percent mortality. In the tabulation of data, the insect species are abbreviated as follows: Housefly (HF), Mexican Bean Beetle (MB), and Southern Armyworm (SA).

Examples 1–3 were subjected to the aforedescribed insecticide tests. Test concentrations and results are set forth in the Table.

TABLE

| COMPOUND | RATE (PPM) | HF | MB | SA |
| --- | --- | --- | --- | --- |
| Example 1 | 500 | 100 | 100 | 100 |
| Example 2 | 500 | 100 | 100 | 100 |
| Example 3 | 500 | 100 | 100 | 100 |

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. Insecticidal compounds having the formula:

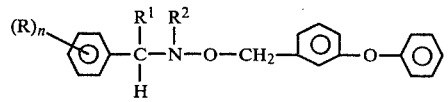

wherein R is halogen (Cl, F, Br), $C_1$–$C_4$ akyl, $NO_2$, $C_1$–$C_4$ alkoxy, $C_1$–$C_4$ alkylthio, cyano, $CF_3$, $CF_3O$, $CF_3S$, $ClF_2$, $CHF_2O$, or $CHF_2S$; n is 0, 1, or 2; $R_1$ is $C_1$–$C_4$ alkyl, $C_3$–$C_6$ cycloalkyl, alkyl substituted $C_3$–$C_6$ cycloalkyl, or $C_2$–$C_4$ alkenyl; and $R^2$ is cyano, carbamoyl, N–$C_1$–$C_4$ alkylcarbamoyl, or N,N-di $C_1$–$C_4$ alkylcarbamoyl.

2. A compound of claim 1, wherein said compound is 4-chloro-N-(N-methylcarbamoyl)-alpha-cyclopropyl-N-(3-phenoxyphenyl)methoxy)benzenemethanamine.

3. A compound of claim 1, wherein said compound is 4-chloro-N-(N-isopropylcarbamoyl)-alpha-cyclopropyl-N-(3-phenoxyphenyl)methoxy)benzenemethanamine.

4. An insecticidal composition comprising a carrier and an insecticidally effective amount of a compound of claim 1.

5. An insecticidal composition comprising a carrier and an insecticidally effective amount of a compound of claim 2.

6. An insecticidal composition comprising a carrier and an insecticidally effective amount of a compound of claim 3.

7. The method for combatting insects which comprises contacting them with an insecticidally effective amount of a compound of claim 1.

8. The method for combatting insects which comprises contacting them with an insecticidally effective amount of a compound of claim 2.

9. The method for combatting insects which comprises contacting them with an insecticidally effective amount of a compound of claim 3.

* * * * *